United States Patent [19]
Hayashi et al.

[11] Patent Number: 5,698,725
[45] Date of Patent: Dec. 16, 1997

[54] SURFACE TREATING AGENT FOR GLASS FIBER SUBSTRATES

[75] Inventors: Masayuki Hayashi; Makoto Iwai, both of Chiba Prefecture, Japan

[73] Assignee: Dow Corning Toray Silicone Co., Ltd., Tokyo, Japan

[21] Appl. No.: 697,995

[22] Filed: Sep. 4, 1996

[30] Foreign Application Priority Data

Sep. 14, 1995 [JP] Japan .................. 7-262124

[51] Int. Cl.$^6$ .................. C07F 7/08; C07F 7/10
[52] U.S. Cl. .............. 556/413; 556/424; 556/425; 428/391; 523/205; 523/209
[58] Field of Search .................. 556/413, 425, 556/424; 428/391; 523/205, 209

[56] References Cited

U.S. PATENT DOCUMENTS

| | | | |
|---|---|---|---|
| 3,700,711 | 10/1972 | Berger et al. | 556/413 |
| 3,734,763 | 5/1973 | Plueddemann | 117/72 |
| 3,946,060 | 3/1976 | Metcalf et al. | 556/413 |
| 4,088,668 | 5/1978 | Metcalf et al. | 556/413 |
| 5,126,467 | 6/1992 | Itagaki et al. | 556/413 |

FOREIGN PATENT DOCUMENTS 47551  7/1993  Japan .

*Primary Examiner*—Paul F. Shaver
*Attorney, Agent, or Firm*—Robert L. McKellar

[57] ABSTRACT

This invention relates to treating agents, glass fiber substrates treated with such agents, and the use of such treated glass fiber substrates in molded, glass fiber reinforced resins that are suited to copper clad laminates, composite base materials, printed wiring boards such as mass lamination boards, and, in particular, multilayer printed wiring boards.

4 Claims, 1 Drawing Sheet

SURFACE TREATING AGENT FOR GLASS FIBER SUBSTRATES

This invention relates to treating agents, glass fiber substrates treated with such agents, and the use of such treated glass fiber substrates in molded, glass fiber reinforced resins that are suited to copper clad laminates, composite base materials, printed wiring boards such as mass lamination boards, and, in particular, multilayer printed wiring boards.

PRIOR ART

After glass fiber substrates such as glass cloth, glass tape, glass mats and glass paper have been impregnated with thermosetting resins such as unsaturated polyester resins, epoxy resins, phenol resins, polyimide resins and polyamide resins, they are thermoset. The molded glass fiber reinforced fibers that are obtained are used for various applications and they are particularly suited for use as printed wiring boards.

In order to impregnate glass fiber substrates sufficiently with thermosetting resins and in order to increase the adhesiveness of the thermosetting resin to the glass substrate, the glass fiber substrate is generally subjected to surface treating with a silane coupling agent such as 3-aminopropyltrimethoxysilane, 3-aminopropyltriethoxysilane, N-(2-aminoethyl)-3-aminopropyltrimethoxysilane, 3-anilinopropyltrimethoxysilane, 3-glycidoxypropyltrimethoxysilane, 2-(3,4-epoxycyclohexyl) ethyltrimethoxysilane, 3-methacryloxypropyltrimethoxysilane, hydrochlorides of trimethoxysilanes as indicated by the formula:

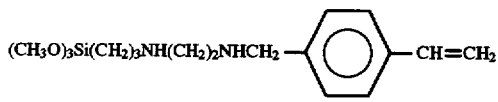

as disclosed in Japanese Patent Disclosure No. 48-20609 (1973), hydrochlorides of trimethoxysilanes as indicated by the formula:

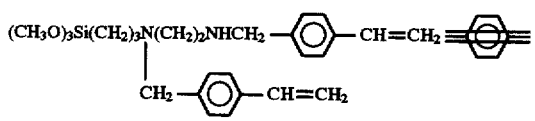

as disclosed in Japanese Patent Disclosure No. 5-47551 (1993), and hydrochlorides of trimethoxysilanes as indicated by the formula:

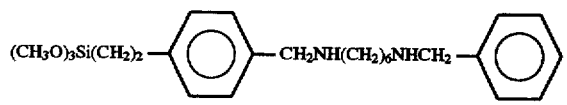

as disclosed in Japanese Patent Disclosure No. 5-65538 (1993).

However, glass fiber substrates that have been subjected to surface treating with these silane coupling agents still do not have sufficient capacity for impregnation with thermosetting resins and sufficient adhesiveness. In particular, when molded glass fiber reinforced resins are used as printed wiring boards and when these boards are subjected to solder treating by hand soldering, drag soldering, dip soldering, wave soldering or reflow soldering at 240° to 260° C., or hot air treating at 300° to 400° C., there are the problems of exfoliation between the glass fibers as a result of insufficient impregnation of the thermosetting resin in the glass fiber substrate, i.e., measling and crazing, exfoliation in the interior of the molded object as a result of poor adhesiveness between the glass fiber substrate and the thermosetting resin, i.e., delamination and exfoliation in the interior of the molded object accompanied by swelling in the surface, i.e., blistering.

Problems the Invention is Intended to Solve

The inventors arrived at this invention as a result of intensive studies of the aforementioned problems.

Specifically, the objective of this invention is to provide molded glass fiber reinforced resins of superior solder heat resistance, prepregs for preparing these molded objects, glass fiber substrates of superior thermosetting resin impregnation capacity for the purpose of preparing these prepregs, and a surface treating agent for glass fiber substrates for the purpose of preparing these substrates.

Means for Solving the Problems and Action

The surface treating agents for glass fiber substrates of this invention are characterized in that they comprise an organosilicon compound having the general formula

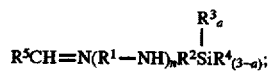

a partially hydrolyzed condensate or a reaction mixture thereof, that is obtained by subjecting an alkoxysilane containing an amino group having the general formula:

 (I)

wherein, $R^1$ and $R^2$ are the same or different divalent hydrocarbon groups, $R^3$ is a monovalent hydrocarbon group, $R^4$ is an alkoxy group, n has a value of 0, 1 or 2 and a has a value of 0, 1 or 2, or a partially hydrolyzed condensate thereof, to a dehydration condensation reaction with an aldehyde as indicated by general formula:

$$R^5-CHO \qquad (II)$$

wherein, $R^5$ is a substituted or unsubstituted aryl group.

The glass fiber substrate of this invention is further characterized in that it is subjected to surface treating by the aforementioned surface treating agent.

The prepreg of this invention is further characterized in that the aforementioned substrate is impregnated with a thermosetting resin.

The molded glass fiber reinforced resin of this invention is further characterized in that the aforementioned prepreg is thermoset.

Detailed Description of the Surface Treating Agent

These surface treating agents are comprised of an organosilicon compounds, partially hydrolyzed condensates, or reaction mixtures thereof, that are obtained by subjecting an alkoxysilane containing an amino group as indicated by general formula (I):

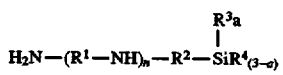

or a partially hydrolyzed condensate thereof, to a dehydration condensation reaction with an aldehyde as indicated by general formula (II): $R^5CHO$ by the following reaction:

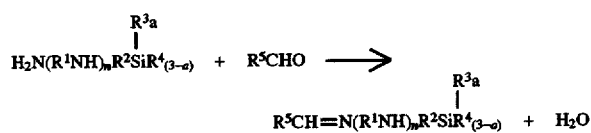

A glass fiber substrate material that has been subjected to surface treating with this substance has superior affinity to thermosetting resins, for which reason there is good capacity for impregnation with and adhesiveness to thermosetting resins and the molded glass fiber reinforced resins can be endowed with superior solder heat resistance.

In the aforementioned general formula (I), $R^1$ and $R^2$, which may be the same or different, can be, for example, alkylene groups such as methylene, ethylene, propylene, butylene, pentylene and hexylene, alkaryl or aralkyl groups such as methylphenylene, ethylphenylene, propylphenylene, phenylmethylene, phenylethylene and phenylpropylene groups. Dialkylarylene groups such as dimethylphenylene, methylethylphenylene, methylpropylphenylene, ethylmethylphenylene and diethylphenylene groups. Alkylene groups are preferable and it is particularly desirable for $R^1$ to be an ethylene group and $R^2$ to be a propylene group. $R^3$ in the formula is a monovalent hydrocarbon group, for example, an alkyl group such as methyl, ethyl, propyl, butyl, pentyl or a hexyl group, an aryl group such as phenyl, tolyl and xylyl, an alkenyl group such as a vinyl, allyl, butenyl, pentenyl, or a hexenyl group or an aralkyl group such as benzyl or a phenethyl group. It is particularly desirable for it to be a methyl group. $R^4$ in the formula is an alkoxy group, for example, a methoxy, ethoxy, propoxy, butoxy, pentoxy group, or a methoxyethoxy group. It is particularly desirable for it to be a methoxy group or an ethoxy group. n in the formula has a value of 0, 1 or 2, with 0 or 1 being particularly desirable. In the formula, a has a value of 0, 1 or 2, with 0 being particularly desirable.

The alkoxysilane containing an amino group as indicated by general formula (I) can be, for example, 3-aminopropyltritrimethoxysilane, 3-aminopropylmethyldimethoxysilane, 3-aminopropyldimethylmethoxysilane, 3-aminopropyltriethoxysilane, 3-aminopropylmethyldiethoxysilane, N-(2-aminoethyl)-3-aminopropyltrimethoxysilane, N-(2-aminoethyl)-3-aminopropylmethyldimethoxysilane, p-(trimethoxsilyl)aniline, N-(m-aminophenyl)-3-aminopropyltrimethoxysilane, N-(6-aminohexyl)-3-aminopropyltrimeihoxysilane and N-{N-(2aminoethyl)-2-aminoethyl}-3-aminopropylmethoxysilane. Of these, 3-aminopropyltrimethoxysilane, 3-aminopropyltriethoxysilane and N-(2-aminoethyl)-3-aminopropyltrimethoxysilane are particularly desirable.

In the aforementioned general formula (II), $R^5$ is a substituted or unsubstituted aryl group. The substituted group in this aryl group may be, for example, an alkenyl group such as a vinyl group or an alkenyl group, an alkyl group such as a methyl group, an ethyl group, a propyl group or a t-butyl group, a halogen atom such as a fluorine atom, a chlorine atom or a bromine atom, an alkoxy group such as a methoxy group, an ethoxy group or a propoxy group, a trifluoromethyl group, a nitro group or a cyano group. $R^5$ may be, for example, a phenyl group, a tolyl group, a xylyl group, a naphthyl group, an anthranyl group, a vinylphenyl group, a chlorophenyl group, a bromophenyl group, methoxyphenyl group, a nitrophenyl group, a cyanophenyl group or a trifluoromethylphenyl group, with phenyl groups and vinylphenyl groups being particularly desirable.

The aldehydes that may be represented by general formula (II) include, for example, benzaldehyde, tolualdehyde, vinylbenzaldehyde, 1-naphthaldehyde, 2-naphthaldehyde, anthracene-9-aldehyde, chlorobenzaldehyde, bromobenzaldehyde, trifluoromethylbenzaldehyde, nitrobenzaldehyde, cyanobenzaldehyde and anisaldehyde. Benzaldehyde and cyanobenzaldehyde are particularly desirable.

The surface treating agent is prepared by a dehydration condensation reaction between the alkoxysilane containing an amino group as indicated by the aforementioned general formula (I) or a partially hydrolyzed condensate thereof and the aldehyde as indicated by the aforementioned general formula (II). A method of preparing this surface treating agent is a method, for example, in which the aforementioned alkoxysilane containing an amino group or a partial hydrolysate thereof and the aforementioned aldehyde are subjected to a dehydration condensation reaction in an inert gas atmosphere such as argon gas, helium gas or nitrogen at normal pressure and at room temperature or heated to 150° C. The quantity of the aforementioned aldehyde relative to the aforementioned alkoxysilane containing an amino group or the partially hydrolyzed condensate thereof that is introduced in this reaction should be 0.1 to 10 moles per 1 mole of nitrogen atoms in the aforementioned alkoxysilane containing an amino group or the partially hydrolyzed condensate thereof. The method for removing the water produced by this reaction may be, for example, a method in which a dehydrating agent is added to the reaction system or a method in which the water that is produced is removed from the reaction system by azeotropic distillation using an organic solvent.

The dehydration condensation reaction can be performed in the absence of a solvent. However, the reaction system can also be diluted with an organic solvent. The solvents that can be used include, for example, alcohol solvents such as methanol, ethanol, i-propanol and t-butanol, hydrocarbon solvents such as toluene, xylene, cyclohexene, n-hexene and n-heptane, halogenated hydrocarbon solvents such as chloroform, carbon tetrachloride and trichloroethylene, ether solvents such as ethyl ether, tetrahydrofuran and ethylene glycol diethyl ether and ester alcohols such as ethyl acetate, butyl acetate and amyl acetate. These solvents can be used individually or in mixtures of two or more.

The progress of the dehydration condensation reaction can be confirmed from the formation of bonds as represented by the formula >C=N— by infrared spectrochemical analysis and $^{13}$C— nuclear magnetic resonance spectrum analysis of the reaction mixture. The reaction mixture that is obtained may also be distilled and purified as required. The surface treating agent that is obtained in this way may be an identifiable organosilicon compound, it may be an organosilicon compound of which the organosilicon compound has partially undergone hydrolysis and a condensation reaction or it may be a reaction mixture comprised of an organosilicon compounds or partially hydrolyzed condensates thereof and unreacted raw materials. The fact that this organosilicon compound has partially undergone hydrolysis and a condensation reaction can be confirmed from the formation of bonds as indicated by the formula Si—O—Si and of bonds as indicated by the formula Si—OH by $^{29}$Si-nuclear magnetic resonance spectrum analysis.

The identifiable organosilicon compounds that are prepared in this way can include, for example, N-benzylidene-3-aminopropyltrimethoxysilane, N-benzylidene-3-aminopropyltriethoxysilane, N-(N'-benzylidene-2-aminoethyl)-3-aminopropyltrimethoxysilane, N-(p-vinylbenzylidene)-3-aminopropyltrimethoxysilane, N-(vinylbenzylidene)-3-aminopropyltriethoxysilane and N-{N'-(p-vinylbenzylidene)-2-aminoethyl}-3-aminopropyltrimethoxysilane. Examples of the surface treating agents of this invention include these organosilicon compounds, partially hydrolyzed condensates of these organosilicon compounds, partially hydrolyzed condensates of these organosilicon compounds and of the raw material alkoxysilanes containing amino groups and combinations of mixtures of these organosilicon compounds and the raw material alkoxysilanes containing amino groups.

A Detailed Description of the Glass Fiber Substrates

The glass fiber ubstrates of this invention are characterized in that they are subjected to a surface treating with the aforementioned surface treating agents. These substrates include, for example, E-glass, which is an inorganic alkali glass belonging to the category of lime-aluminoborosilicate glass, A-glass, which is a soda-lime glass, and, in addition C-glass, L-glass, D-glass and S-glass. Of these, E-glass is particularly desirable. The components of the substrate may be, for example, $SiO_2$, $CaO$, $Al_2O_3$. The substrate can be, for example, glass cloth, glass mat, glass tape, glass paper, roving and roving cloth. This glass cloth and glass tape can be obtained, for example, by interweaving yarns comprised of several hundred glass strands (filaments) of 5 to 15 μm as the warp threads and the woof threads by means of plain weaving, perforation plain weaving, twilling, satin weaving and leno weaving.

Methods that can be used in preparing this substrate include, for example, methods in which the substrate is immersed in the surface treating agent and methods in which the surface treating agent is applied by spraying to the substrate. At this time, in order to remove the fiber size that is used in manufacturing the glass fiber substrate, the substrate should be subjected to heat cleaning in advance. The aforementioned surface treating agent is generally used diluted with an organic solvent or water. For example, it may be used in concentrations of 0.01 to 5.0 wt %, and, preferably in concentrations of 0.1 to 2.0 wt %. When the surface treating agent is used as an aqueous solution, the use of an aqueous solution of acetic acid prepared to a pH of 3 to 5 is desirable. In addition, the use of an alcohol containing 5 to 99 wt % of water or of an aqueous solution of alcohol containing acetic acid is also desirable. After the surface treating agent has been affixed to the substrate, the substrate should be dried in order to eliminate the organic solvent or water contained in the surface treating agent. In order to achieve a sufficient surface treating of the substrate it should be subjected to a heating treatment at 60° to 150° C.

Detailed Description of a Prepreg of This Invention

The prepreg of this invention is characterized in that the aforementioned glass fiber substrate is impregnated with a thermosetting resin. This thermosetting resin may be a phenol resin, a xylene resin, a urea resin, a melamine resin, a polyester resin, an alkyd resin, an epoxy resin, a silicone resin, a BT (bismaleimide-triazine) resin, a polyimide resin or a polyamide resin. Other components, for example, hardeners, hardening promoters, flame retardants and inorganic fillers, may be compounded with these thermosetting resins.

The methods that can be used for making the prepreg include methods in which the substrate is immersed in the thermosetting resin, the thermosetting resin is applied by spraying to the glass fiber substrate or the glass fiber substrate is impregnated with the thermosetting resin, after which the substrate is dried and methods in which the impregnated thermosetting resin is hardened by heating until it is in a partially hardened state.

Detailed Description of the Molded Glass Fiber Reinforced Resin

The molded objects of this invention are characterized in that they are obtained by thermosetting the aforementioned prepregs. This molded object may be obtained by thermosetting the prepreg in a single layer or it may be obtained by laminating and thermosetting the prepreg in multiple layers. When the molded object is to be used as a printed wiring board, copper foil may be established on the surface. When it is to be used for multilayer printed wiring boards, it should be laminated and thermoset in a state in which the inner layer circuits are inserted into the prepreg.

The method that is generally used to make this molded object is a method in which the aforementioned prepreg is laminated in a single layer or multiple layers and in which it is thermoset by heating and pressing. The pressure when the prepreg is heated and pressed should be 5 to 100 kg/cm2.

The molded glass fiber reinforced resin of this invention exhibits the properties of good impregnation capacity of and adhesiveness of the thermosetting resins to the glass fiber substrates, for which reason they can be used satisfactorily as printed wiring boards of superior solder heat resistance and the printed wiring boards can be laminated in thin layers.

EXAMPLES

The molded fiber reinforced resins were made as follows.

Method of Making Molded Fiber Reinforced Resins

The glass fiber substrate was immersed in a thermosetting resin, after which the excess thermosetting resin was removed. Then, the prepreg was made by heating and hardening the substrate to a partially hardened state. Sixteen of these prepregs were laminated and copper foil of 35 μm in thickness was overlaid on the top and bottom. Stainless steel plates having a thickness of about 2 mm were placed at the top and bottom and the material was thermoset for 1 hour at 130° C. under an increased pressure of 40 kg/cm2, with a laminated glass reinforced resin plate of 4 mm in thickness having copper foil affixed to both faces.

The impregnation capacity of the thermosetting resin in the glass fiber substrate and the solder heat resistance of the molded glass fiber reinforced resin were evaluated as follows.

Impregnation Capacity of the Thermosetting Resin in the Glass Fiber Substrate

The impregnation capacity of the thermosetting resin in the glass fiber substrate was observed visually. When impregnation capacity was good, an evaluation of O was made; when impregnation capacity was ordinary, an evaluation of δ was made, and when impregnation capacity was poor, an evaluation of x was made.

The copper foil of the laminated glass fiber reinforced resin plate made by the aforementioned method was removed by etching, after which the external appearance was observed visually. When it appeared transparent, an evaluation of O was made; when there were white spots in place, an evaluation of δ was made, and, when large numbers of white spots were seen, an evaluation of x was made.

A soldering iron at 270° C. was pressed for 10 seconds against a laminated plate having a good external appearance, after which the external appearance of the laminated plate was observed. When measling or blistering did not occur, an evaluation of O was made; and, when measling or blistering occurred, an evaluation of x was made.

Solder Heat Resistance of Glass Fiber Reinforced Resin

The copper foil of the laminated glass fiber reinforced resin plate made by the aforementioned method was removed by etching, after which two laminated plates having good external appearance were treated for 8 hours and 24 hours, respectively, at 121° C. and 23 atmospheres. Following that, these laminated plates were immersed for 20 seconds in a solder bath at 260° C. and observations were made of the external appearance of these laminated plates. The proportion of the area in regions in which delamination or blistering had occurred (destroyed area) on these laminated plates was observed.

Example of Synthesis 1

A silane, 3-aminopropyltriethoxysilane (67.6 gm) was introduced into a four-necked flask equipped with a thermometer, a stirrer and a cooler, after which a reaction was carried out at room temperature as 32.4 g of benzaldehyde was added dropwise. Following that, the water that was produced by the reaction was separated, after which the reaction mixture was heated, with a transparent liquid being obtained by distillation. When the liquid was analyzed by infrared spectrochemical analysis (hereafter, IR), $^{13}C-$ nuclear magnetic resonance spectrum analysis (hereafter, NMR) and $^{29}Si-$NMR, bonds as indicated by the formula >C=N— were confirmed and this liquid was identified as N-benzylidene-3-aminopropyltriethoxysilane.

Example of Synthesis 2

A silane, N-(2-aminoethyl)-3-aminopropyltrimethoxysilane (67.7 gm.) was introduced into a four-necked flask equipped with a thermometer, a stirrer and a cooler and 32.3 g of benzaldehyde was then introduced at room temperature. Next, this mixture was stirred for 5 hours at 40° C., with a pale yellow transparent viscous liquid being prepared. When this liquid was analyzed by IR, $^{13}C-$ and $^{29}Si-$NMR, bonds as indicated by the formula >C=N— and bonds as indicated by the formula Si—O—Si were confirmed and it was confirmed that this viscous liquid was an organosilicon compound of which the principal component was N-(N'-benzylidene-2-aminoethyl)-3-aminopropyltrimethoxysilane and a partially hydrolyzed condensate thereof.

Example of Synthesis 3

A silane, 3-aminopropyltriethoxysilane (25 gm.) was introduced into a four-necked flask equipped with a thermometer, a stirrer and a cooler and 15.0 g of vinyl benzaldehyde was then introduced at room temperature. Following that, the mixture was stirred for 5 hours at 40° C., with a pale yellow transparent viscous liquid being prepared. When this liquid was analyzed by IR, $^{13}C-$ and $^{29}Si-$NMR, bonds as indicated by the formula >C=N— and bonds as indicated by the formula Si—O—Si were confirmed and it was confirmed that this viscous liquid was an organosilicon compound of which the principal component was N-vinylbenzylidene-3-aminopropyltriethoxysilane and a partially hydrolyzed condensate thereof. Next, 60.0 g of methanol was added to this viscous liquid, with a methanol solution being prepared.

Example of Synthesis 4

A silane, N-(2-aminoethyl)-3-aminopropyltrimethoxysilane (25.1 gm.) was introduced into a four-necked flask equipped with a thermometer, a stirrer and a cooler and 14.9 g of vinyl benzaldehyde was then introduced at room temperature. Next, this mixture was stirred for 5 hours at 40° C., with a pale yellow transparent viscous liquid being prepared. When this liquid was analyzed by IR, $^{13}C-$ and $^{29}Si-$NMR, bonds as indicated by the formula >C=N— and bonds as indicated by the formula Si—O—Si were confirmed and it was confirmed that this viscous liquid was an organosilicon compound of which the principal component was N-(N'-vinylbenzylidene-2-aminoethyl)-3-aminopropyltrimethoxysilane and a partially hydrolyzed condensate thereof. Next, 60.0 g of methanol was added to this viscous liquid, with a methanol solution being prepared.

Examples 1–4

Plain weave nonalkaline glass fiber cloth (EP18 as described in JIS R 3414) was subjected to heat cleaning, after which it was immersed in pH 4 aqueous solutions of acetic acid in which was compounded the surface treating agents for glass fiber substrates prepared in Examples of Synthesis 1 through 4 in amounts of 0.5 wt %. Following this, the substrates were squeezed with a mangle and were then heated and dried for 7 minutes in an oven at 130° C., to prepare surface treated glass substrates.

Then, a hardenable epoxy resin comprised of 80 parts by weight of bisphenol A epoxy resin (epoxy equivalent=480; Epikote 1001, brand name of a product manufactured by Yuka Shell Epoxy Company), 20 parts by weight of bisphenol A epoxy resin (epoxy equivalent=190; Epikote 828, brand name of a product manufactured by Yuka Shell Epoxy Company), 3 parts by weight of dicyandiamide, 0.2 parts by weight of benzyl dimethylamine, 40 parts by weight of dimethylformamide and 40 parts by weight of methylethyl ketone was prepared. The substrate was impregnated with this hardening epoxy resin, after which it was heated for 5 minutes at 150° C., by which means this hardening epoxy resin was converted to a partially hardened state and to prepare a prepreg with a hardenable epoxy resin content of 40 wt %.

A laminated glass fiber reinforced epoxy resin plate having copper foil attached to both faces was prepared using this prepreg.

Table 1 shows the impregnation capacity of this hardenable epoxy resin with this glass fiber substrate and the solder heat resistance of the laminated glass fiber reinforced epoxy resin plate.

Comparative Example 1

Plain weave nonalkaline glass fiber cloth (EP18 as described in JIS R 3414) was subjected to heat cleaning, after which it was immersed in pH 4 aqueous solutions of acetic acid in which N-(N'-vinylbenzyl-2-aminoethyl)-3-aminopropyltrimethoxysilane hydrochloride was compounded in an amount of 0.5 wt %. Following this, the substrate was squeezed with a mangle and was then heated and dried for 7 minutes in an oven at 130° C., to prepare a glass fiber substrate that had been subjected to surface treating.

Then, using this substrate, the hardenable epoxy resin was made into a partially hardened state by heating for 5 minutes at 150° C. in the same way as in Example 1 to prepare a prepreg with a hardenable epoxy resin content of 40 wt %.

A laminated glass fiber reinforced epoxy resin plate having copper foil attached to both faces was prepared using this prepreg.

Table 1 shows the impregnation capacity of this hardenable epoxy resin to the glass fiber substrate and the solder heat resistance of the laminated glass fiber reinforced epoxy resin plate.

Comparative Example 2

Plain weave nonalkaline glass fiber cloth (EP18 as described in JIS R 3414) was subjected to heat cleaning, after which it was immersed in pH 4 aqueous solutions of acetic acid in which N-(N'-vinylbenzyl-2-aminoethyl)-3-aminopropyltrimethoxysilane was compounded in an amount of 0.5 wt %. Following this, the substrate was squeezed with a mangle and was then heated and dried for 7 minutes in an oven at 130° C., with a glass fiber substrate that had been subjected to surface treating being prepared.

Using this substrate, the hardenable epoxy resin was made into a partially hardened state by heating for 5 minutes at 150° C. in the same way as in Example 1 to prepare a prepreg with a hardenable epoxy resin content of 40 wt %.

A laminated glass fiber reinforced epoxy resin plate having copper foil attached to both faces was prepared using this prepreg.

Table 1 shows the impregnation capacity of this hardenable epoxy resin with this glass fiber substrate and the solder heat resistance of the laminated glass fiber reinforced epoxy resin plate.

TABLE I

| | PROPERTY | | | | |
|---|---|---|---|---|---|
| | A | B | C | D | E |
| Invention Examples | | | | | |
| 1 | O | O | O | <1% | 8% |
| 2 | O | O | O | <1% | 8% |
| 3 | O | O | O | <1% | 8% |
| 4 | O | δ | O | <1% | 8% |
| Comparative Examples | | | | | |
| 1 | δ | δ | X | 6% | 35% |
| 2 | O | δ | X | 6% | 33% |

A = Impregnation capacity of hardenable epoxy resin to the glass fiber substrate. External appearance of prepreg.
B = External appearance of the laminated glass fiber reinforced epoxy resin plate.
C = Occurence of measling and blistering.
D = Solder heat resistance of the laminated glass fiber reinforced eooxy resin plate. Proportion of destroyed area after 8 hours of treatment.
E = Proportion of destroyed area after 24 hours of treatment.

Molded glass fiber reinforced resins of this invention are characterized in that they are of superior solder heat resistance, the prepregs of this invention are characterized in that they can be used to make these molded objects, the glass fiber substrates of this invention are characterized in that they exhibit superior impregnation capacity in thermal hardenable resins and that they can be used to make this kind of prepregs and the surface treating agents for glass fiber materials of this invention are characterized in that they can be used to make this kind of glass fiber substrates.

Figure 1:
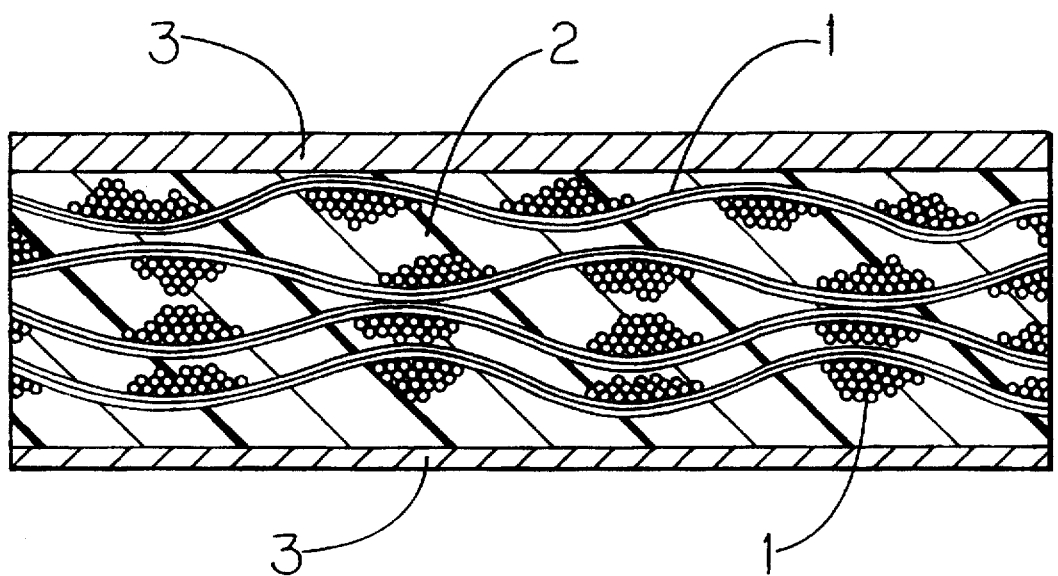
FIG. 1 is a cross-sectional view of the laminated glass fiber reinforced resin plate that was made in the example. A portion of the glass fiber substrate is omitted in the figure. The number 1 is the glass fiber substrate, the number 2 is the hardened epoxy resin, and number 3 is the copper foil.

We claim:

1. A surface treating agent for glass fiber substrates comprising an organosilicon compound selected from the group consisting of:

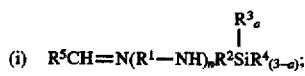

(ii) a hydrolyzate of (i), (iii) a condensate of (i), (iv) a mixture of (i) and (ii), (v) a mixture of (i) and (iii) and, (vi) a mixture of (i), (ii) and (iii), wherein, $R^1$ and $R^2$ are the same or different divalent hydrocarbon groups, $R^3$ is a monovalent hydrocarbon group, $R^4$ is an alkoxy group, $R^5$ is a substituted or unsubstituted aryl group, n has a value of 0, 1 or 2 and a has a value of 0, 1 or 2.

2. A glass fiber substrate treated with an organosilicon compound of claim 1.

3. A prepreg consisting of a glass fiber substrate claimed in claim 2 impregnated with a thermosetting resin.

4. A molded glass fiber reinforced resin obtained by thermosetting the prepreg claimed in claim 3.

* * * * *